United States Patent [19]
Jayaweera et al.

[11] Patent Number: 5,280,250
[45] Date of Patent: Jan. 18, 1994

[54] METHOD AND APPARATUS FOR MEASURING ζ POTENTIAL OF A SUBSTANCE AT HIGH TEMPERATURE

[75] Inventors: Palitha Jayaweera, Mountain View; Samson Hettiarachchi, Menlo Park, both of Calif.

[73] Assignee: Electric Power Research Institute, Inc., Palo Alto, Calif.

[21] Appl. No.: 769,174

[22] Filed: Sep. 30, 1991

[51] Int. Cl.$^5$ .................. G01N 27/27; G01N 27/416; G01N 27/60
[52] U.S. Cl. .................................... 324/452; 324/438; 324/453
[58] Field of Search ............... 324/438, 449, 452, 453, 324/454, 457

[56] References Cited

U.S. PATENT DOCUMENTS

| | | | |
|---|---|---|---|
| 3,306,320 | 2/1967 | Bond | 324/453 X |
| 3,368,144 | 2/1968 | Gerdes | 324/453 |
| 3,502,965 | 3/1970 | Gerdes et al. | 324/453 |
| 5,059,909 | 10/1991 | O'Brien | 324/453 X |

OTHER PUBLICATIONS

Parks, G. A. Chem Rev. 65:117 (1965) "The Isoelectric Points of... and Aqueous Hydroxo Complex Systems", pp. 177-198.

Van Wagenen, R. A. et al. J. Coll. Interface Sci. 76:305 (1980), "Flat Plate Streaming Potential Investigations: Hydrodynamics 'and Electrokinetic Equivalency" pp. 305-314.

Primary Examiner—Gerard R. Strecker
Attorney, Agent, or Firm—Flehr, Hohbach, Test, Albritton & Herbert

[57] ABSTRACT

The invention describes a novel device to measure ζ-potentials of substances at high temperatures. The device involves packing the substance to be measured into a "RULON" (polytetrafluoroethylene including a heat resistant filler, e.g., fiberglass, quartz, asbestos, ceramic fibers or mica) column and passing an electrolyte through the column. Measurements are taken across the column to measure streaming potential and the pressure drop, and a sensor in series with the column to measure the pH of the electrolyte. ζ-potentials are calculated from slopes of the plots of streaming potential (ΔE) vs. differential pressure (ΔP) using a computer controlled data acquisition system.

40 Claims, 4 Drawing Sheets

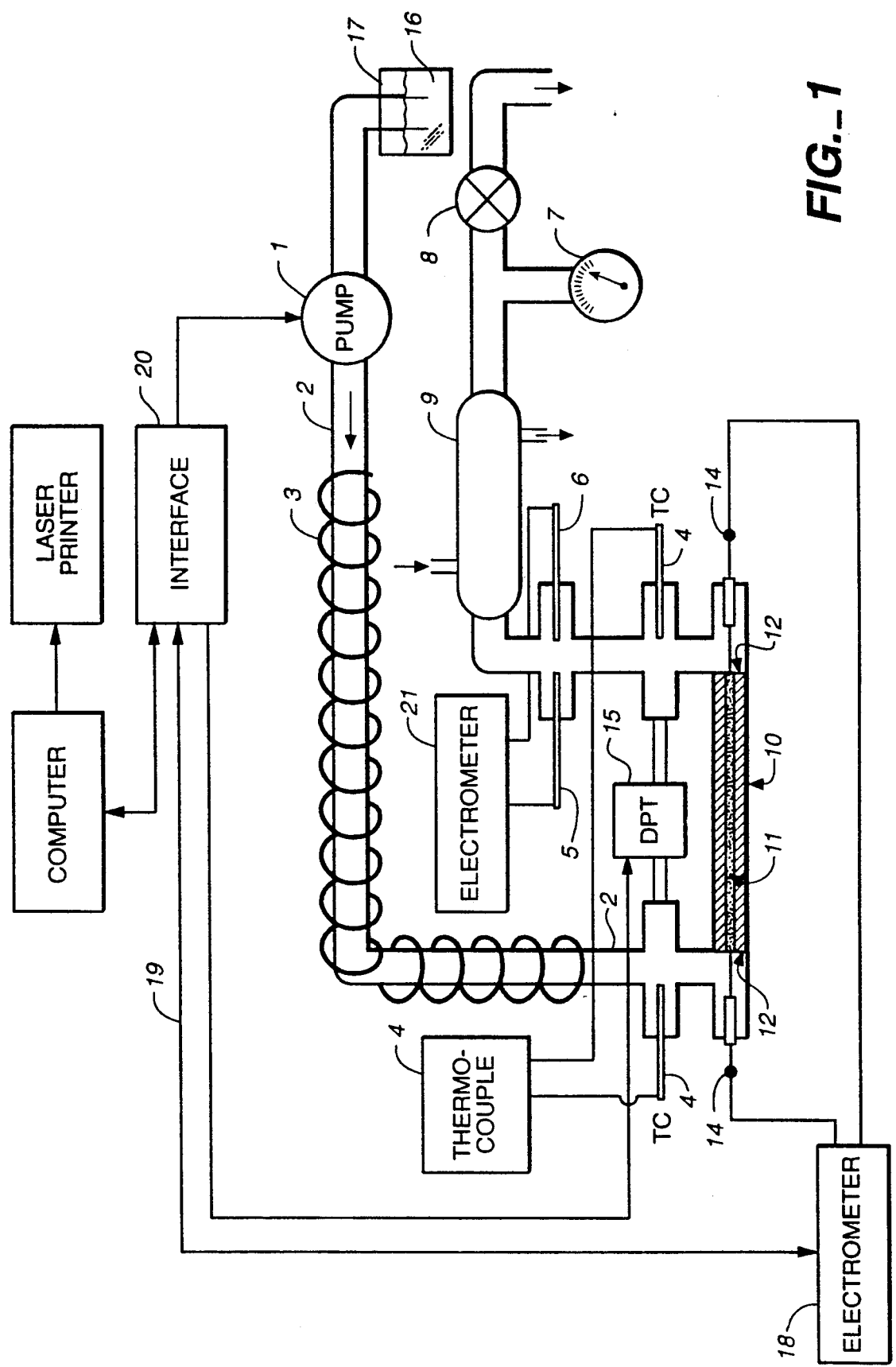
FIG._1

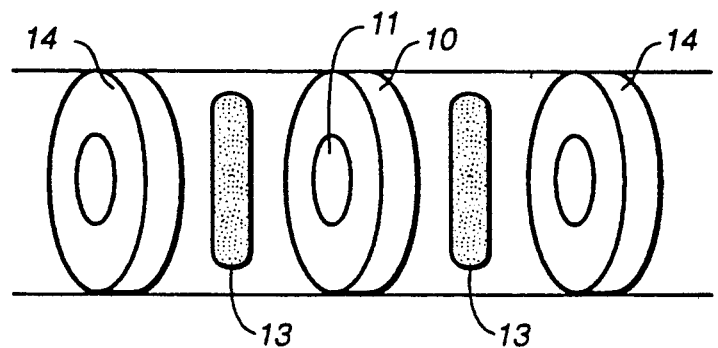
FIG._2
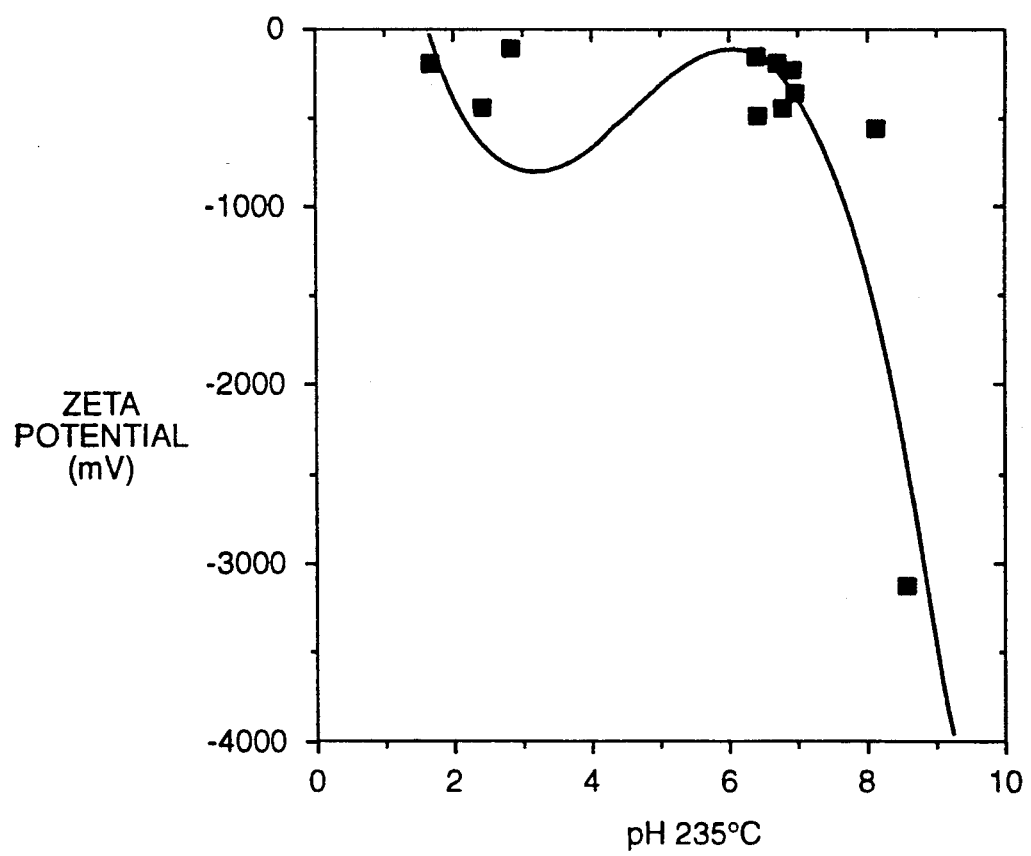
FIG._3

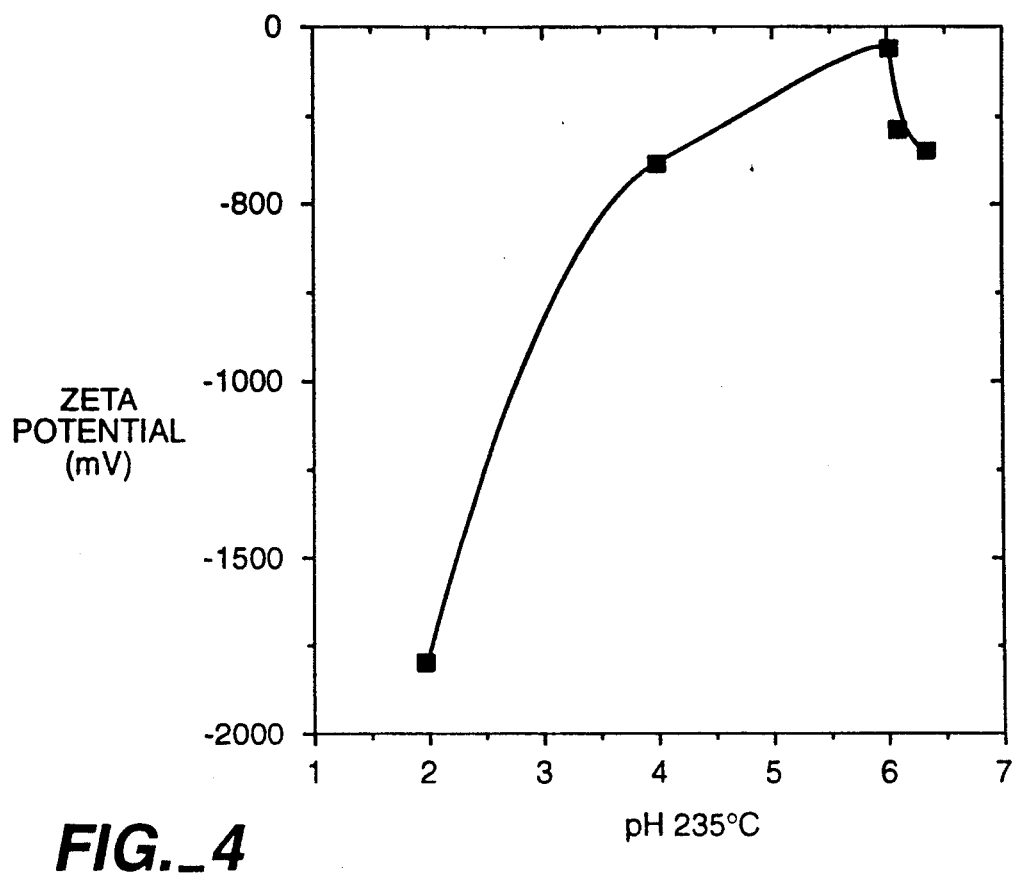
FIG._4
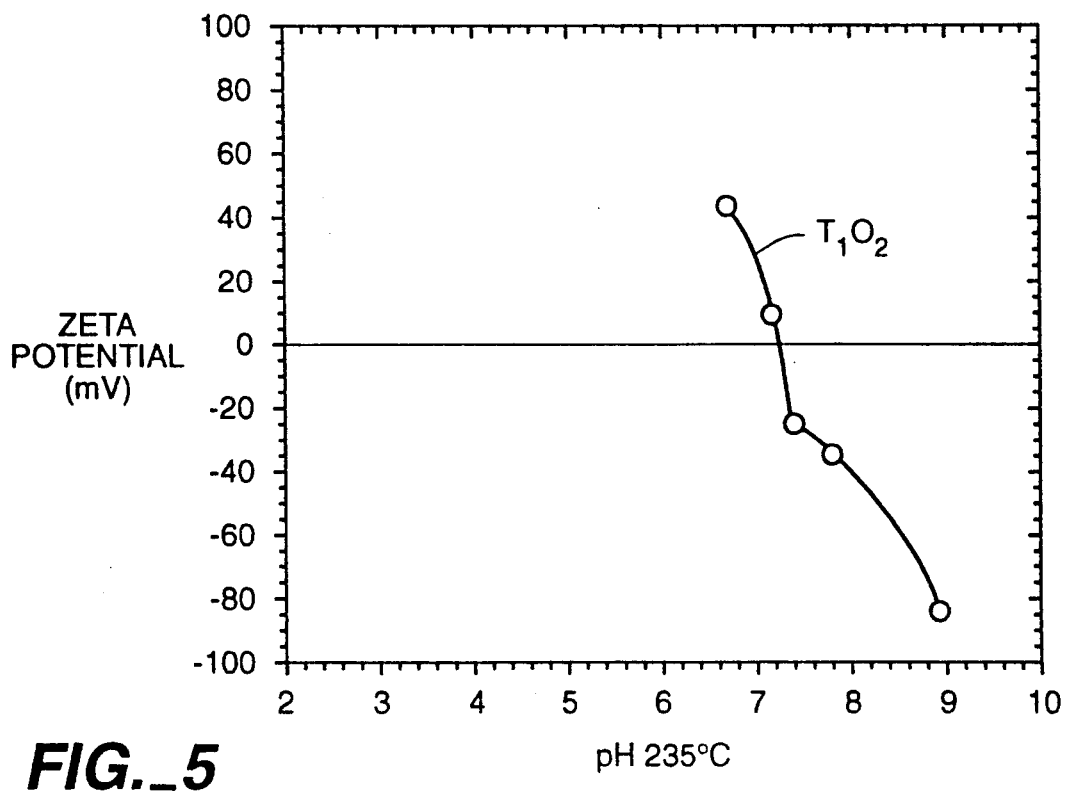
FIG._5

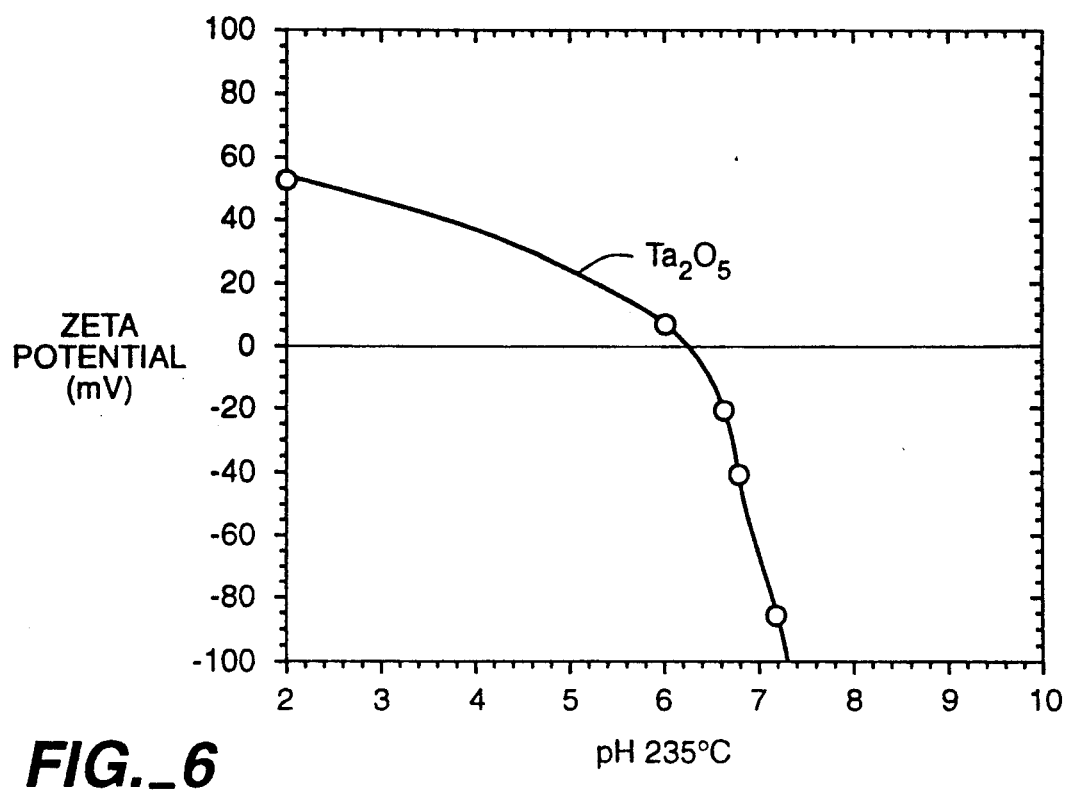
FIG._6
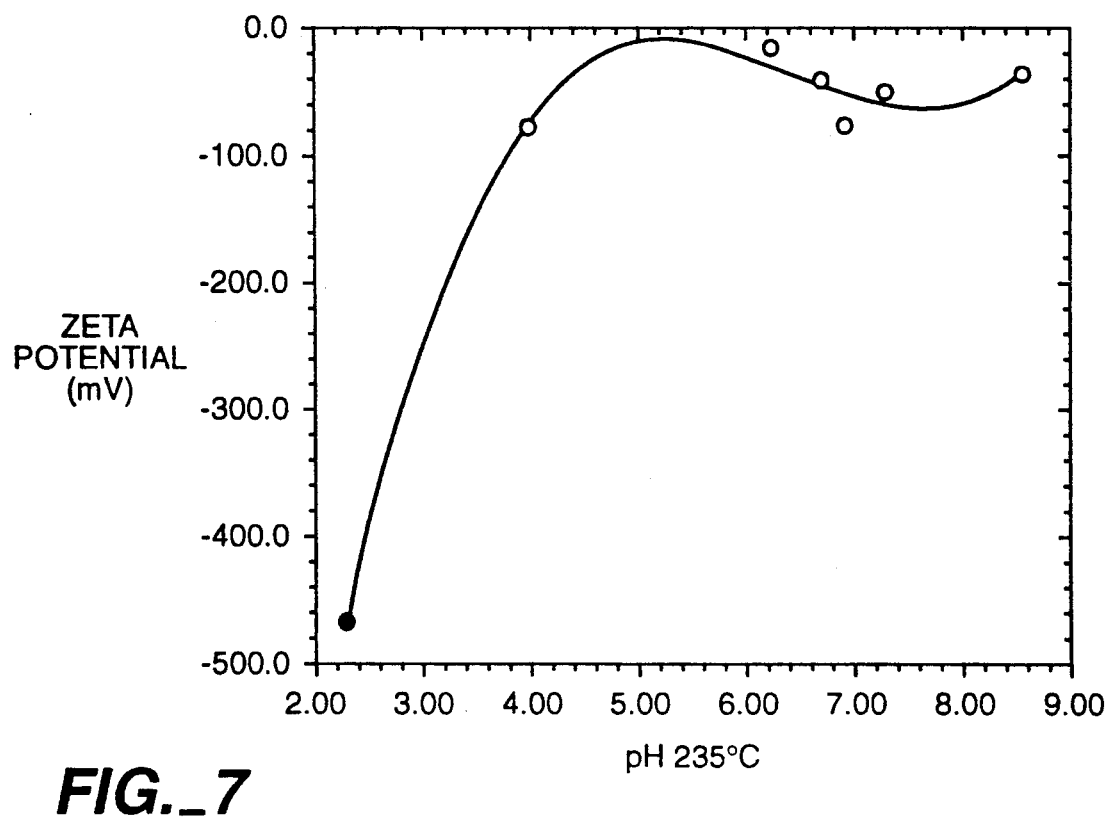
FIG._7

METHOD AND APPARATUS FOR MEASURING ζ POTENTIAL OF A SUBSTANCE AT HIGH TEMPERATURE

FIELD OF THE INVENTION

This invention relates to a device for measurement of ζ-potentials at high temperature. These measurements may be used, for example, to determine the surface charge of particles.

BACKGROUND OF THE INVENTION

Electrokinetic phenomena involve either the movement of charged particles through a continuous medium or the movement of a continuous medium over a charged surface. The four principal electrokinetic phenomena are electrophoresis, electroosmosis, streaming potential and sedimentation potential. These phenomena are related to one another through the zeta potential, ζ, of the electrical double layer which exists in the neighborhood of the charged surface.

The distribution of electrolyte ions in the neighborhood of a negatively charged surface and the variation of potential, ψ, with distance from the surface are well known in the art (see, for example, Zeta Potential in Colloid Science Principles and Applications; R.J. Hunter; Academic Press, N.Y. (1988)). Two different layers of ions appear to be associated with the charged surface. The layer of ions immediately adjacent to the surface is called the inner Helmholtz (IH) layer; the second layer of ions is the outer Helmholtz (OH) layer.

Ions of the IH layer are held to the charged surface by a combination of electrostatic attraction, specific adsorption forces and chemical bonds. The thickness, δ, of this layer is assumed to be equal to the ionic radius of the specifically adsorbed ionic species.

The second layer of ions is the OH layer. The boundary between the two layers is the limiting inner Helmholtz plane. The ions outside the OH layer are acted upon only by electrostatic forces and thermal motions of the liquid environment (Brownian motion), and they form a diffuse atmosphere of opposite charge to the net charge at the OH plane. The net charge density of the ion atmosphere of the diffused layer decreases exponentially with distance from the limiting OH plane.

The diffused layer forms one half of an electrical double layer, and the charged surface plus the inner and outer Helmholtz layers form the other half. The effective distance of separation 1/k between the two halves of the double layer is determined by the concentration of electrolyte (ionic strength). For an electrolyte of univalent ions in water at 25° C. (77° F.), the relationship for 1/k from the Debye-Huckel theory is described by an equation.

$$\frac{1}{k} = \left(\frac{E_0 DRT}{2000 F^2}\right)^{-\frac{1}{2}} \cdot \frac{1}{\sqrt{I}} \qquad (1)$$

where
- $E_o$ is the permittivity of free space
- D is the dielectric constant
- R is the gas constant
- T is the absolute temperature
- F is the Faraday constant
- I is the ionic strength, defined as:

$$I = \tfrac{1}{2}\Sigma(C_i Z_i^2) \qquad (2)$$

where,
- $C_i$ is the concentration, and
- $Z_i$ is the valency of the ionic species.

The potential ψ on the surface of the charged particle, decreases linearly with increasing distance x in the region of the inner and outer Helmholtz layers.

In the region of the diffused layer, Φ decreases exponentially with increasing distance x.

In electrokinetic phenomena, a displacement occurs at some plane (plane of shear) between the charged surface and its atmosphere of ions. The position of the slipping plane is known to be located in the OH layer. The potential of the plane of shear is the ζ-potential. From the theories of Gouy and Chapman, for spherical particles a second equation holds:

$$\zeta = \frac{q}{Da}\left(\frac{1}{1+k}\right) \qquad (3)$$

Where $$q = \frac{q_e}{4kE_0}, \qquad (4)$$

$q_e$ is the charge on the particle.

Here 1/k is the effective thickness of the double layer, D the dielectric constant of the liquid, and a the particle's radius at the plane of shear. For flat surfaces, a fifth equation holds, where e is the charge per unit area of surface:

$$\zeta = \frac{4\pi e}{Dk} \qquad (5)$$

Thus, the equations 2 and 3 above show that the ζ-potential is determined by the net charge at the plane of shear and 1/k, the effective thickness of the ion atmosphere. In turn, the ζ-potential controls the rate of transport between the charge surface and the adjacent liquid. The relationship between rate of transport $v_E$ and the ζ-potential which is valid for all four electrokinetic phenomena is given by a sixth equation, where $v_E$ is the velocity of the liquid at a large distance from the charged surface, E is the electric field strength (V/cm), and η is the viscosity of the liquid.

$$v_E = \frac{D\zeta E}{4\pi\eta} \qquad (6)$$

The conditions for validity of this sixth equation are that the double layer thickness (1/k) must be small compared to the radius of curvature of the surface; the substance of the surface must be nonconducting; and the surface conductance of the interface must be negligible.

The equation which relate ζ-potential to the streaming potential may be obtained from this sixth equation by use of Poiseuille's law for laminar flow through a capillary. For electrophoresis and sedimentation potential, $v_E$ is the velocity of the particles. E is the applied field strength for electrophoresis, whereas it is the gradient of potential developed by the sedimentation of charged particles in the sedimentation effect.

The effect of electrolyte concentration on the ζ-potential is also well known. Characteristically, an increase in electrolyte concentration produces a decrease in $\zeta$-potential, and ions of high charge of opposite sign to that of the surface can completely reverse the sign of the $\zeta$-potential. The explanation for these two effects is also well known: an increase in electrolyte concentration reduces $\zeta$-potential by reducing $1/k$, as indicated by equations 1-3 and 6, given above. Reversal of charge by ion adsorption occurs in the double layer and this gives rise to a $\zeta$-potential of opposite sign to the original value.

Knowledge of high temperature zeta potentials and point of zero charge (pzc), as well as other physicochemical properties, is important in advanced ceramics manufacture, particle deposition, removal of charged species, coating adhesion, microbial deposition in cooling systems and in many other technologically and economically important applications where surface charge of particles plays a role.

Although $\zeta$-potential measurements have been determined in the past, they have been confined to measurement at ambient temperatures or to temperatures $<95°$ C. High temperature $\zeta$-potential measurement has been very complex due to the high pressures involved and the difficulties associated with sample retention within the high temperature loop and its isolation from the all metal loop and the inability to measure pH at high temperatures.

Using the device of this invention, it is possible to measure zeta potentials and hence the pzc's of various oxides and other materials at high temperature and pressure. The invention is unique—no methods are currently available to determine high temperature zeta potentials of materials. The lack of a reliable method to determine the pH of aqueous systems at high temperature has prevented the experimental determination of zeta potentials.

Thus, it is an object of this invention to provide an apparatus and method for measuring $\zeta$-potentials at high temperature. In a preferred embodiment, the apparatus is computer controlled.

DESCRIPTION OF THE DRAWINGS

FIG. 1 shows the experimental arrangement used for zeta potential measurement. In the presently preferred embodiment, automated computer control of the measuring process is accomplished using components shown in the FIGURE and software developed to monitor and control the system.

FIG. 2 is an enlarged and expanded view (central figure) of the "RULON" section of the loop. As explained in the text, the substance or surface to be measured is held in place by platinum screens and, if necessary, "TEFLON" (polytetrafluoroethylene) filters as the electrolyte flows through and contacts the substance or surface.

FIG. 3 shows the results of zeta potential measurement vs. pH at 235° C. for PdO.

FIG. 4 shows results of zeta potential measurement vs. pH at 235° C. for $WO_3$.

FIG. 5 shows results of zeta potential measurement vs. pH at 235° C. for $TiO_2$.

FIG. 6 shows results of zeta potential measurement vs. pH at 235° C. for $Ta_2O_5$.

FIG. 7 shows results of zeta potential measurement vs. pH at 235° C. for $Nb_2O_5$.

DETAILED DESCRIPTION OF THE INVENTION

The novel apparatus developed for high temperature $\zeta$-potential measurements is shown in FIG. 1 and in FIG. 2. A solution 16, preferably an electrolyte, from storage source 17 is pumped into the loop by a commercial HPLC pump 1. The loop 2 is made of $\frac{1}{4}''$ and $\frac{1}{8}''$ stainless steel tubing. Heating tapes 3 wrapped around the stainless steel tubing are controlled by commercial temperature controllers and thermocouples (TC) 4 that sense the temperature at both ends of a "RULON" (polytetrafluoroethylene including a heat resistant filler, e.g., fiberglass, quartz, asbestos, ceramic fibers or mica) column 10. A streaming potential is generated by passing the electrolyte 16 through the "RULON" column 10 packed with a specimen powder substance 11 to be studied. The streaming potential generated across the column is measured by an electrometer 18, as shown in FIG. 1, interfaced to a computer, via a IEEE 488 general purpose interface bus (GPIB) 19 and an ACM2-12-8A interface card 20 (Strawberry Tree, Inc.). The interface card together with the GPIB 19 function as the computer interface for data acquisition and experiment control. A differential pressure transducer 15 is used to measure the pressure drop across the column. High temperature pH (from about 100° C. to about 300° C.) of the electrolyte is calculated from the measurement of potential (via electrometer 21) between a yttria-stabilized zirconia (YSZ) pH electrode 5 and an external pressure balanced reference electrode (EPBRE) 6. The pressure of the system (from about 10 psi to about 1200 psi) is measured by a pressure gauge 7 and pressure is maintained by adjustable pressure release valve 8. The solution is cooled to room temperature by passing it through a cooling water jacket 9 before it is discharged from the system.

The substances to be studied are packed into a "RULON" column 10 which is tightly fitted inside the stainless steel tubing 2. "RULON" provides the electrical isolation of the substance powder 11 from the stainless steel tubing wall. Powder is held in the column by Pt screens 12 that also serve as electrodes for measuring streaming potentials. For very fine powders, "TEFLON" filters 13 are used in addition to Pt screens. Contacts to the electrodes are made through "RULON" ferrules 14. The column region 10 of the loop is thermally well insulated to avoid heat losses an maintain the column at the required temperature. "RULON" columns 10 are made to different lengths such that they provide easily measurable pressure drops across the column.

In a newer design, as shown in FIG. 2, the column lengths can be changed simply by changing the thickness of the center "RULON" ring 10. The powder 11 is packed in the center opening of the ring and the three rings 10 are held tightly by pipe fittings that also provide the high pressure seal. Nominal thicknesses of rings are about 3/32" for outer electrode holder rings and about 3/16" for center ring. Ring O.D. and I.D. are about 3/8" and 3/16", respectively. The outer stainless steel casing 2 supports the, "RULON" column 10 to take the high pressure. The "RULON" column 10 can be easily modified to accommodate solid surfaces to study surface charge of coatings. Thus, both powders and solid surfaces can be used to determine the $\zeta$-potential of the material of interest. When solid surfaces are used, their distance of separation should be small (10-100 mils) so that adequate pressure drops along the length of the separation can be attained by varying the liquid flow.

Design of the column and the electrode contacts are key parts of the high temperature $\zeta$-potential measuring system. Experimental difficulties at high temperature and pressure have prevented measurements of $\zeta$-potentials above about 95° C. The novel design of the column and electrode contacts make it possible to measure $\zeta$-potential of materials from around 0° C. up to and beyond the supercritical temperature of water.

In a presently preferred embodiment, automated computer control of the zeta potential measuring process is used. The presently preferred computer interface with the loop, to control the fluid flow rate and to acquire data is presented for illustration purposes in FIG. 1.

EXAMPLE $\zeta$-potentials of various oxides at high temperature have been measured using the above-described apparatus. To better describe the use of this apparatus, the following example is provided, which is not intended to in any way limit the scope of this invention.

Measurement of the high temperature $\zeta$-potential of oxides as a function of pH to determine their pzc's and the sign of the surface charge was carried out. PdO and WO$_3$ (Aldrich Chemicals) powders were separately placed in the rulon column, held in place by platinum screens (and additionally "TEFLON" filters). Although a variety of electrolytes (such as KCl, KNO$_3$ or any other inert electrolyte, at concentrations in the range from about $10^{-3}$ to about $10^{-4}$M) could be used, $10^{-3}$M KNO$_3$ was circulated through the measuring loop, contacting and passing through the PdO and WO$_3$ powders in the rulon column.

The pressure in the loop was held at approximately 600 psi; the temperature of the electrolyte in the column was held at about 235° C. for the course of the measurements. The pH of the electrolyte solution was also measured at the test temperature. $\zeta$-potential is calculated from the slope of the graph of streaming potential ($\Delta E$) vs. differential pressure ($\Delta P$).

$$\frac{\Delta E}{\Delta P} = \frac{E_0 D r^2 R}{4\eta l} \cdot \zeta \tag{7}$$

R = Resistance of the powder packed column
r = radius of the column
l = length of the column.

The entire system of varying the flow rate of the HPLC pump and the acquisition of $\Delta E$ and $\Delta P$ data was under computer control.

Using this method, both PdO and WO$_3$ show negative $\zeta$-potentials at 235° C. over the pH range 2 to 9 and 2 to 6.5, respectively, (FIGS. 3 and 4). Thus, it is clear that at the operating pH's of the materials tested, pH5.6 and pH7.2, both PdO and WO$_3$ remain negatively charged.

FIGS. 5-7 illustrate the results of similar experimental measurements performed on other potential coating materials.

What is claimed is:

1. An apparatus for measuring the $\zeta$-potential of a substance at high temperature comprising:

a. a measurement loop defining a passageway formed to permit passage of an electrolyte at a high temperature and a high pressure therethrough;
 b. pump means capable of moving said electrolyte from a storage source through said passageway;
 c. a temperature control device operably coupled to said measurement loop in a manner capable of raising and lowering the temperature of said electrolyte in said passageway in response to monitoring the temperature of said electrolyte;
 d. a measuring column defining a chamber formed and dimensioned to receive said substance therein, said chamber in communicating relation with said passageway in a manner permitting fluid contact of said electrolyte with said substance from an entrance into said chamber to an exit from said chamber, said column further formed to provide electrical isolation of said substance from said measurement loop at said high temperature and pressure, and including electrodes positioned proximate said entrance and said exit of said chamber for measuring a streaming potential across said substance after contact with said electrolyte; and
 e. a pressure measuring device operably coupled to said passageway and positioned in parallel with said column along said passageway for measurement of a differential pressure across a portion of said passageway before and after said electrolyte has contacted said substance.

2. An apparatus of claim 1, wherein said pump means is a high-pressure liquid chromatography (HPLC) pump.

3. An apparatus of claim 1, wherein said measurement loop includes tubing providing said passageway.

4. An apparatus of claim 3, wherein said tubing comprises stainless steel tubing.

5. An apparatus of claim 1, wherein said electrolyte is selected from the group consisting of KCl, KNO$_3$, NaNO$_3$, NaCl or any inert electrolyte.

6. An apparatus of claim 1, further including a pH measuring device positioned across a portion of said passageway and capable of measuring the pH of said electrolyte at said high temperature.

7. An apparatus of claim 6, wherein said pH measuring device is positioned along said passageway downstream from said measuring column.

8. An apparatus of claim 1, wherein said high temperature of said electrolyte is in the range from about 100° C. to about 300° C.

9. An apparatus of claim 1, wherein said high pressure of said electrolyte is in the range from about 10 psi to about 1200 psi.

10. An apparatus of claim 3, wherein said temperature control device comprises heating means in heat communication with a portion of said passageway, cooling means in cooling communication with another portion of said passageway, and a temperature monitoring device.

11. An apparatus of claim 1, wherein said pressure measuring device comprises a different pressure transducer capable of measuring said differential pressure.

12. An apparatus of claim 10, wherein
 said heating means comprises heating tape in conductive contact with said tubing at a position upstream from said column,
 said cooling means comprises a cooling jacket in conductive contact with said tubing at a positioned downstream from said column, and said temperature monitoring device is provided by a first thermocontroller positioned proximate one end of said column, and a second thermocontroller positioned proximate an opposite end of said column.

13. An apparatus of claim 12, wherein said cooling jacket is a cooling water jacket.

14. An apparatus of claim 6, wherein said pH measuring device comprises a yttria-stabilized sirconia pH electrode, and an external pressure balanced reference electrode capable of providing a reference potential for pH measurement of said electrolyte.

15. An apparatus of claim 1, wherein said measuring column comprises an electrical insulating ring defining said chamber, and formed and dimensioned to be positioned inside said passageway in a manner providing said electrical insulation of said substance from said measurement loop.

16. An apparatus of claim 15, wherein said ring comprises "RULON".

17. An apparatus of claim 15, wherein said column further includes a first Pt screen positioned proximate said entrance into said column chamber, and a second Pt screen positioned proximate said exit from said column chamber, said first and said second Pt screens co-operating to tightly support said substance therebetween in said chamber.

18. An apparatus of claim 17, wherein said Pt screens are electrically conductive and serve as said electrodes.

19. An apparatus of claim 18, wherein said column further includes a first screen holder ring urging said first Pt screen against said column, and a second screen holder ring urging said second Pt screen against said column, aid screen holder rings each being formed to electrically insulate said Pt screens, respectively, from said measurement loop.

20. An apparatus of claim 18, wherein said column further includes a first "TEFLON" filter positioned between said first screen holder and said column, and a second "TEFLON" filter positioned between said second screen holder and said column.

21. An apparatus of claim 18, wherein said column further includes "RULON" ferrules electrically isolating contacts to each electrode from said measurement loop.

22. An apparatus of claim 1, further including computation means operably coupled to said measuring column, for input of said streaming potential thereto, and operably coupled to said pressure measuring device, for input of said differential pressure thereto, said computation means calculating the $\zeta$-potential of said substance through use of said streaming potential and said differential pressure in a predetermined equation.

23. An apparatus of claim 1, wherein said column is thermally insulated.

24. A method for measuring the $\zeta$-potential of a substance at a high temperature and pressure in a $\zeta$-potential measuring apparatus, said apparatus comprising a measurement loop defining a passageway formed to permit passage of an electrolyte at a high temperature and a high pressure therethrough, pump means capable of moving said electrolyte from a storage source through said passageway, and a temperature control device operably coupled to said measurement loop in a manner capable of raising and lowering the temperature of said electrolyte in said passageway in response to monitoring the temperature of said electrolyte, said method comprising the steps of:

positioning a measuring column, defining a chamber formed and dimensioned to receive said substance therein, along and in communicating relation with said passageway in a manner permitting fluid contact of said electrolyte with said substance therein from an entrance into said chamber to an exit from said chamber;

electrically isolating said substance from said measurement loop at said high temperature and pressure through placement of said substance in said chamber;

measuring a streaming potential across said substance, after contact of said substance with said electrolyte, by positioning electrodes proximate said entrance and said exit of said chamber;

measuring a differential pressure across a portion of said passageway at positions before and after said electrolyte has contacted said substance through a pressure measuring device operably coupled to said passageway and positioned in parallel with said column along said passageway; and calculating said $\zeta$-potential measurement of said substance by factoring said differential pressure measurement and said steaming potential measurement into a predetermined equation.

25. A method of claim 24, wherein said electrolyte is selected from the group consisting of Kcl, KNO3, NaCl, NaNO3 or any inert electrolyte.

26. A method of claim 24, wherein said predetermined equation is provided by $(\Delta E)/(\Delta P) = -((E_0 D r^2 R)/(4\eta 1))\zeta$, wherein $\Delta E$ = the streaming potential, $\Delta P$ = the differential pressure, $E_0$ = the permittivity of free space, D = the dielectric constant of the median, r = the radius of the column, R = the resistance of the substance packed column, $\eta$ = the viscosity of the electrolyte, and 1 = the length of the column.

27. A method of claim 24, wherein said measurement loop includes tubing providing said passageway.

28. A method of claim 24 further including the step of:

measuring the pH of the electrolyte across a portion of said passageway through a pH measuring device capable of measuring the pH at said high temperature and positioned along said passageway.

29. A method of claim 24, wherein said column comprises an electrical insulating ring defining said chamber, and formed and dimensioned to be positioned inside said passageway in a manner providing said electrical insulation of said substance from said measurement loop.

30. A method of claim 24, wherein said measuring column further includes a first Pt screen positioned proximate said entrance into said column chamber, and a second Pt screen positioned proximate said exit from said column chamber, said first and said second Pt screens cooperating to tightly support said substance therebetween in said chamber.

31. A method of claim 30, wherein said Pt screens are comprised of an inert electrically conductive material and serve as said electrodes.

32. A method of claim 31, wherein said column further includes a first screen holder ring urging said first Pt screen against said column, and a second screen holder ring urging said second Pt screen against said column, said screen holder rings each being formed to electrically insulate said Pt screens, respectively, from said measurement loop.

33. A method of claim 24, wherein said pressure is in the range from about 10 psi to about 1200 psi.

34. A method of claim 24, wherein said temperature is in the range from about 100° C. to about 300° C.

35. A method of claim 24, wherein said predefined temperature is adjustable by means of a temperature control device 4.

36. A method of claim 24, wherein said pressure measuring device comprises a differential pressure transducer.

37. A method of claim 24, wherein said pH measuring device comprises a yttria-stabilized zirconia (YSZ) pH electrode.

38. A method of claim 24, wherein said pH measuring device comprises a yttria-stabilized zirconia (YSZ) pH electrode, and an external pressure balanced reference electrode (EPBRE) capable of providing a reference potential for measuring the pH of said electrolyte when the temperature of said electrolyte at high temperature.

39. A method of claim 24, wherein said calculating step is accomplished by computation means operably coupled to said measuring column, for input of said streaming potential thereto, and operably coupled to said pressure measuring device, for input of said differential pressure thereto.

40. A method of claim 32, wherein said column further includes a first "TEFLON" filter positioned between said first screen holder and said column, and a second "TEFLON" filter positioned between said second screen holder and said column.

* * * * *